(12) United States Patent
Cumming

(10) Patent No.: US 7,985,253 B2
(45) Date of Patent: *Jul. 26, 2011

(54) HYDROLIC ACCOMMODATING INTRAOCULAR LENS

(75) Inventor: J. Stuart Cumming, Laguna Beach, CA (US)

(73) Assignee: C&C Vision International Limited, Dublin (IE)

( * ) Notice: Subject to any disclaimer, the term of this patent is extended or adjusted under 35 U.S.C. 154(b) by 0 days.

This patent is subject to a terminal disclaimer.

(21) Appl. No.: 11/924,485

(22) Filed: Oct. 25, 2007

(65) Prior Publication Data

US 2008/0269887 A1 Oct. 30, 2008

Related U.S. Application Data

(63) Continuation-in-part of application No. 11/458,886, filed on Jul. 20, 2006, which is a continuation-in-part of application No. 11/297,232, filed on Dec. 7, 2005, now abandoned.

(51) Int. Cl.
*A61F 2/16* (2006.01)

(52) U.S. Cl. ............... 623/6.13; 623/6.34; 623/6.44; 623/6.51

(58) Field of Classification Search .............. 623/6.13, 623/6.32, 6.34, 6.37, 6.44
See application file for complete search history.

(56) References Cited

U.S. PATENT DOCUMENTS

| 4,174,543 A | 11/1979 | Kelman |
| 4,244,060 A | 1/1981 | Hoffer |
| 4,254,509 A | 3/1981 | Tennant |
| 4,254,510 A | 3/1981 | Tennant |
| 4,298,996 A | 11/1981 | Barnet |
| 4,304,012 A | 12/1981 | Richard |
| 4,409,691 A | 10/1983 | Levy |
| 4,424,597 A | 1/1984 | Schlegel |
| 4,441,217 A | 4/1984 | Cozean, Jr. |
| 4,477,931 A | 10/1984 | Kelman |
| 4,573,998 A | 3/1986 | Mazzocco |
| 4,585,457 A | 4/1986 | Kalb |
| 4,605,411 A | 8/1986 | Fedorov et al. |
| 4,629,462 A | 12/1986 | Feaster |
| 4,664,666 A | 5/1987 | Barrett |
| 4,673,406 A | 6/1987 | Schlegel |
| 4,704,123 A | 11/1987 | Smith |
| 4,718,904 A | 1/1988 | Thornton |
| 4,738,680 A | 4/1988 | Herman |
| 4,753,655 A | 6/1988 | Hecht |

(Continued)

FOREIGN PATENT DOCUMENTS

EP 0208546 A 1/1987

(Continued)

OTHER PUBLICATIONS

Archimede Busacca, Ciliary Muscle Physiology Studied by Gonioscopy, Annals of Oculistics, vol. CLXXXVIII, Jan. 1955 (English Translation), 13 pages.

(Continued)

*Primary Examiner* — David H. Willse

(74) *Attorney, Agent, or Firm* — Orrick, Herrington & Sutcliffe LLP

(57) ABSTRACT

An accommodating intraocular lens comprising an optic made from solid silicone and liquid silicone. The optic has a central anterior area or membrane that can vary in radius and thus charge power.

35 Claims, 8 Drawing Sheets

U.S. PATENT DOCUMENTS

| | | |
|---|---|---|
| 4,759,761 A | 7/1988 | Portnoy |
| 4,778,463 A | 10/1988 | Hetland |
| 4,813,955 A | 3/1989 | Achatz et al. |
| 4,816,030 A | 3/1989 | Robinson |
| 4,840,627 A | 6/1989 | Blumenthal |
| 4,842,601 A | 6/1989 | Smith |
| 4,880,427 A | 11/1989 | Anis |
| 4,892,543 A | 1/1990 | Turley |
| 4,932,966 A | 6/1990 | Christie et al. |
| 4,932,968 A | 6/1990 | Caldwell et al. |
| 4,932,970 A | 6/1990 | Portney |
| 4,963,148 A | 10/1990 | Sulc et al. |
| 4,994,082 A | 2/1991 | Richards et al. |
| 5,047,051 A | 9/1991 | Cumming |
| 5,078,742 A | 1/1992 | Dahan |
| 5,141,507 A | 8/1992 | Parekh |
| 5,171,319 A | 12/1992 | Keates et al. |
| 5,171,320 A | 12/1992 | Nishi |
| 5,217,490 A | 6/1993 | Sayano et al. |
| 5,275,624 A | 1/1994 | Hara et al. |
| 5,376,115 A | 12/1994 | Jansen |
| 5,476,514 A | 12/1995 | Cumming |
| 5,496,366 A | 3/1996 | Cumming |
| 5,522,891 A | 6/1996 | Klaas |
| 5,578,078 A | 11/1996 | Nakajima et al. |
| 5,674,282 A | 10/1997 | Cumming |
| 6,051,024 A | 4/2000 | Cumming et al. |
| 6,129,760 A | 10/2000 | Fedorov et al. |
| 6,193,750 B1 | 2/2001 | Cumming |
| 6,197,059 B1 | 3/2001 | Cumming |
| 6,231,603 B1 | 5/2001 | Lang et al. |
| 6,387,126 B1 | 5/2002 | Cumming |
| 6,423,094 B1 | 7/2002 | Sarfarazi |
| 6,494,911 B2 | 12/2002 | Cumming |
| 6,503,276 B2 | 1/2003 | Lang et al. |
| 6,540,353 B1 | 4/2003 | Dunn |
| 6,551,354 B1 | 4/2003 | Ghazizadeh et al. |
| 6,554,859 B1 | 4/2003 | Lang et al. |
| 6,558,419 B1 | 5/2003 | Pham et al. |
| 6,638,305 B2 | 10/2003 | Laguette |
| 6,638,306 B2 | 10/2003 | Cumming |
| 6,767,363 B1 | 7/2004 | Bandhauer |
| 6,786,928 B2 | 9/2004 | Callahan et al. |
| 6,818,158 B2 | 11/2004 | Pham et al. |
| 7,018,409 B2 | 3/2006 | Glick et al. |
| 7,048,760 B2 | 5/2006 | Cumming |
| 7,150,760 B2 | 12/2006 | Zhang |
| 2001/0001836 A1 | 5/2001 | Cumming |
| 2002/0128710 A1 | 9/2002 | Eggleston |
| 2003/0018384 A1 | 1/2003 | Valyunin et al. |
| 2003/0060880 A1 | 3/2003 | Feingold |
| 2003/0060881 A1 | 3/2003 | Glick et al. |
| 2003/0187505 A1 | 10/2003 | Liao |
| 2003/0204254 A1 | 10/2003 | Peng et al. |
| 2004/0002757 A1 | 1/2004 | Lai et al. |
| 2004/0082993 A1* | 4/2004 | Woods ............... 623/6.28 |
| 2004/0082995 A1 | 4/2004 | Woods |
| 2005/0107875 A1 | 5/2005 | Cumming |
| 2006/0116764 A1 | 6/2006 | Simpson |
| 2006/0259140 A1 | 11/2006 | Dell |
| 2007/0021831 A1* | 1/2007 | Clarke ............... 623/6.13 |
| 2007/0129800 A1 | 6/2007 | Cumming |

FOREIGN PATENT DOCUMENTS

| | | |
|---|---|---|
| EP | 0336877 A1 | 10/1989 |
| EP | 0941717 A | 9/1999 |
| GB | 2171912 A | 9/1986 |
| WO | WO 95/06446 | 3/1995 |
| WO | WO 96/15734 A2 | 5/1996 |
| WO | WO 96/25126 A1 | 8/1996 |
| WO | WO 01/97742 A2 | 12/2001 |
| WO | WO 2004/046768 A2 | 6/2004 |
| WO | WO 2007/037180 A1 * | 4/2007 |

OTHER PUBLICATIONS

Archimede Busacca, La Physiologid Du Muscle Ciliarire Etudiee par la Gonioscopie, Annales D'Oculistique, vol. CLXXXVIII, 1st Livraison, Janvier 1955 (French Translation), pp. 1-21.

D. Jackson Coleman, M.D., On the Hydraulic Suspension Theory of Accommodation, Tr. Am. Opth. Soc. vol. LXXXIV, pp. 846-868, 1986.

J. Stuart Cumming, M.D., Accommodating Intra-Ocular Lens Development & Clinical Results, PowerPoint presentation 1999-2000, 14 pages.

Spencer Thornton, "Accommodating in Pseudophakia," Color Atlas of Lens Implantation, Chapter 25, pp. 159-162.

Lee, Judith, "Update on IOLs," Outpatient Surgery (Mar. 2002), printed Oct. 26, 2004 (http://www.outpatientsurgery.net/2002/os03/f4.shtml), 5 pages.

Zhang, Z. et al., "A clinical study of posterior capsular opacification after implantation of foldable intraocular lenses with different edges of optics," Zhonghua Yan Ke Za Zhi 38(10):606-609 (Oct. 2002), printed Oct. 26, 2004 (http://www.ncbi.nlm.nih.gov/entrez/query.fcgi?cmd=Retrieve&db=pubmed&dopt—Abstract&list . . . ), 1 page.

Masket, Samuel, "Continuing Medical Education: Oct. 2003 IOL Edge Design, and PCO Dysphotopsia," Review of Ophthalmology, printed Oct. 26, 2004 (http://www.revophth.com/index.asp?ArticleType=SiteSpec&page=cme/oct03/lesson.htm), 10 pages.

Sabbagh, Leslie, "IOL Design Closes Off PCO," Review of Ophthalmology, printed Oct. 26, 2004 (http://www.revophth.com/index.asp-?page=1_255.htm) vol. No. 10:1 Issue:Jan. 15, 2003; 3 pages.

* cited by examiner

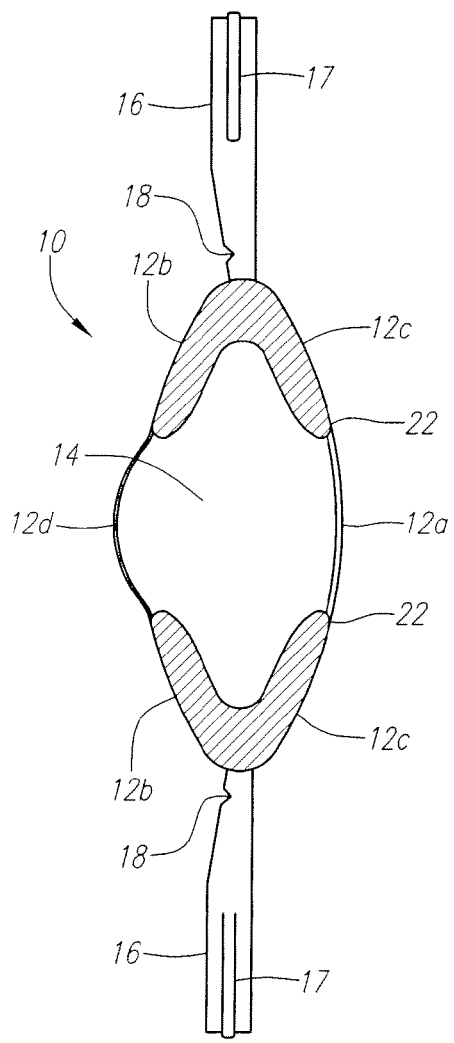 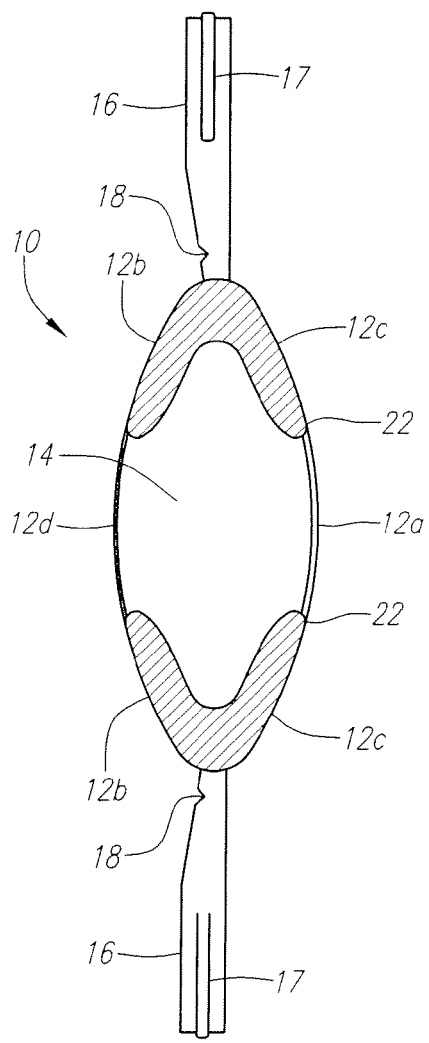
*F I G .   7 A*    *F I G .   7 B*

HYDROLIC ACCOMMODATING INTRAOCULAR LENS

This application is a continuation-in-part of application Ser. No. 11/458,886 filed Jul. 20, 2006, which is a continuation-in-part of Ser. No. 11/297,232 filed Dec. 7, 2005, now abandoned, the disclosures of which are expressly incorporated herein by reference.

BACKGROUND

Intraocular lenses have for many years had a design of a single optic with loops attached to the optic to center the lens and fixate it in the empty capsular bag of the human lens. In the mid '80s plate lenses were introduced, which comprised a silicone lens, 10.5 mm in length, with a 6 mm optic. These lenses could be folded but did not fixate well in the capsular bag, but resided in pockets between the anterior and posterior capsules. The first foldable lenses were all made of silicone. In the mid 1990s an acrylic material was introduced as the optic of lenses. The acrylic lens comprised a biconvex optic with a straight edge into which were inserted loops to center the lens in the eye and fixate it within the capsular bag.

Recently accommodating intraocular lenses have been introduced to the market, which generally are modified plate haptic lenses and, like the silicone plate haptic lenses, have no clear demarcation between the junction of the plate with the optic's posterior surface. A plate haptic lens may be referred to as an intraocular lens having two or more plate haptics joined to the optic.

Flexible acrylic material has gained significant popularity among ophthalmic surgeons. In 2003 more than 50% of the intraocular lenses implanted had acrylic optics. Hydrogel and collamer lenses have also been introduced.

The advent of an accommodating lens which functions by moving along the axis of the eye by repeated flexions somewhat limited the materials from which the lens could be made. Silicone is the ideal material, since it is flexible and can be bent probably several million times without showing any damage. Additionally a groove or hinge can be placed across the plate adjacent to the optic as part of the lens design to facilitate movement of the optic relative to the outer ends of the haptics. On the other hand, some acrylic materials can fracture if they are repeatedly flexed.

An example accommodating lens is a type as disclosed in U.S. Pat. No. 6,387,126 and others in the name of J. Stuart Cumming.

SUMMARY OF THE INVENTION

According to a preferred embodiment of this invention, an accommodating lens comprises a lens with a flexible solid and interior liquid optic, preferably with two or more extended portions from the solid optic which may be plate haptics capable of multiple flexions without breaking, preferably along with fixation and centration features at their distal ends. There may be a hinge or groove across the extended portions adjacent to the optic to facilitate the anterior and posterior movement of the optic relative to the outer ends of the extended portions. On the other hand, the optic may be rigidly attached to the haptics. Also, haptics can be omitted.

According to the present invention the optic is of a foldable, flexible silicone, acrylic, collamer or hydrogel material with an interior of liquid silicone, or other optically clear fluid, and the haptics are of a foldable material that will withstand multiple foldings without damage, e.g., silicone. Preferably, the end of the plate haptics have T-shaped fixation devices and the haptics are hinged to the optic.

The lens of the present invention is made of solid silicone with liquid silicone both of which may have similar or the same refractive indices. The liquid may be any other liquid that is optically clear and has a different refractive index than the solid silicone. It is preferable that the liquid in the optic have a specific gravity the same as or very similar to that of the aqueous solution of the natural eye. The power of the lens can be changed by (1) changing the radius of the solid central posterior portion of the optic, and/or (2) by changing the volume of the liquid silicone in the lens optic, or (3) by changing the refractive index of the liquid either before or after implantation. The posterior surface of the lens is pushed forward by vitreous cavity pressure with constriction of the ciliary muscle. This causes bulging of an anterior membrane of the lens increasing its curvature and thus decreasing the radius of the anterior surface of the lens increasing the lens power for near vision.

The thin anterior membrane may be thicker in its periphery such that an increase in pressure inside the lens will produce a central bulging of the membrane. This structure simulates the structure of the anterior capsule of the human lens and simulates its function. The posterior central optic portion may have additional single or multiple solid spherical components or may be aspherical or toric on its posterior surface. Also, the increase in vitreous cavity pressure can tilt the lens to further facilitate accommodation.

Accordingly, features of the present invention are to provide an improved form of accommodating lens formed from solid and liquid silicone.

BRIEF DESCRIPTION OF THE DRAWINGS

FIGS. 7A, 7B, and 8A-8D illustrate further variations.

DESCRIPTION OF THE PREFERRED EMBODIMENT

Figures 1, 2:
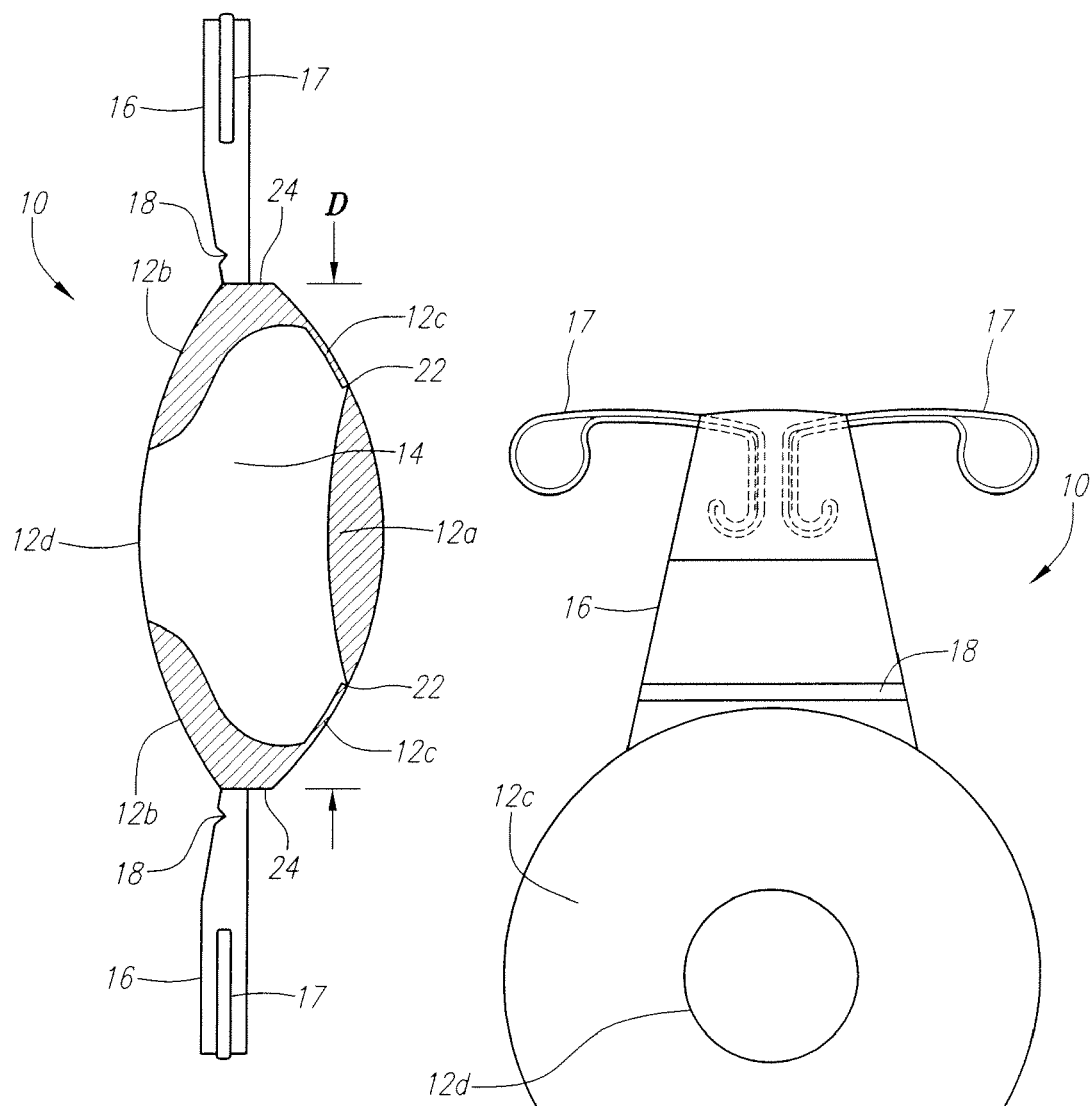
FIG. 1 is a side cross sectional view of the preferred embodiment of the lens of the present invention.
FIG. 2 is a plan view from the anterior side of the lens.
Figure 3:
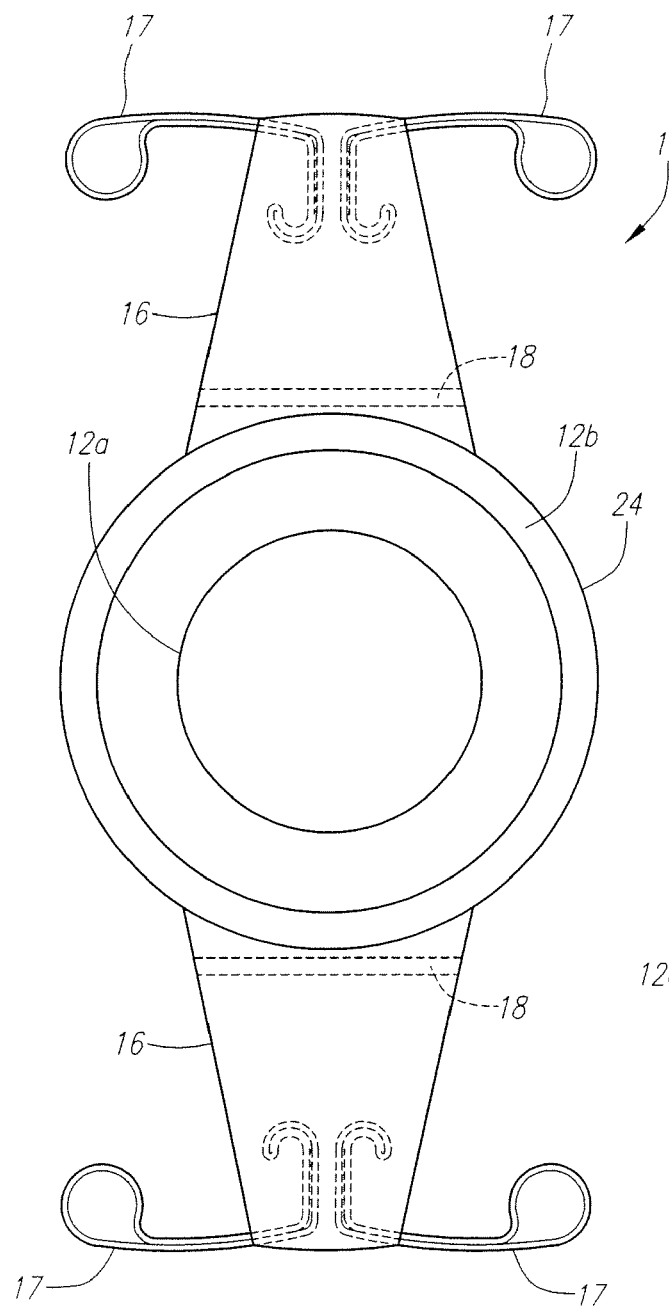
FIG. 3 is a plan view from the posterior side of the lens.

Turning now to the drawings, a preferred embodiment is shown in detail, comprising an intraocular lens with an optic 10 and haptics 16. The optic 10 is formed of two components, namely, a flexible solid portion 12 (12a-12d) preferably made of silicone, collamer, acrylic or hyrdrogel, and an interior liquid preferably silicone portion 14. The portions 12a and 12b are sufficiently solid to prevent deformation of the optic 10 upon implantation into the fibrosed capsular bag of the eye. The flexible extending portions 16 may be plate haptics which are capable of multiple flexations without damage, and formed, for example, of silicone. The optic 10 and haptics 16 preferably are uniplanar, and two or more haptics 16 extend distally from opposite sides of the optic 10. The outer ends of the haptics 16 may include flexible fingers 17 such as disclosed in U.S. Pat. No. 6,387,126 to Cumming. Preferably the edge 24 of the optic is a 360° square edge.

Figure 4:
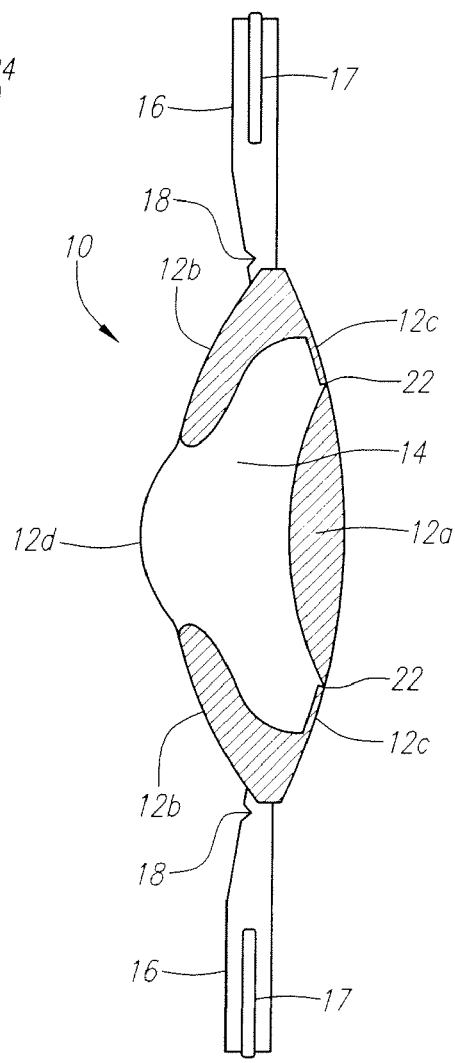
FIG. 4 is a cross-sectional view of the lens like FIG. 1 but showing bulging or increased curvature of an anterior portion of the lens.

The lens 10 includes portions 12a, 12b and 12d of solid silicone and wherein the portion 12c is substantially thinner, and 12d is even thinner than 12c, to enable a degree of flexibility as can be seen in comparing FIG. 1 and FIG. 4. The interior 14 is a liquid and preferably silicone. As is known, the specific gravity of the silicone used in this lens can be the same as or very similar to that of the aqueous solution in the human eye. This results in either no or negligible deformation of the liquid portion of the lens by gravity. The liquid silicone 14 may have the same or similar refractive index as the solid components 12. The solid posterior radius of portion 12a prevents deformation of the posterior refracting surface. The radius of the portions 12a or 12b can be changed, during manufacturing, to select the desired power for the lens. Also, the power can be changed during manufacturing or after implantation by changing the volume or refractive index of the liquid 14 in the lens optic 10.

In accommodating, the posterior surface portion 12a is pushed forward (to the left in FIGS. 1 and 4) by vitreous cavity pressure with constriction of the ciliary muscle. The anterior portion 12d bulges with increased curvature, that is decreased radius, of the anterior portion 12d such as illustrated in FIG. 4.

Example dimensions are 4.5-10.5 mm in overall diameter of portion 12b from D to D in FIG. 1, up to a 5 mm diameter portion 12d, and a 3-6 mm thickness (from right to left) in FIG. 1. A typical thickness for the solid silicone portions 12a and 12b is between 0.5 mm and 1.5 mm. The thickness of the anterior membrane 12d is very thin, preferably about that of a toy balloon, and the thickness of the annulus 12c is approximately two times that thickness to give sufficient flexibility to the solid posterior lens. The thickness at the hinge 18 area can be 0.1 mm. The hinge area 18 can be a "V" shape as shown but can be a square groove. Also, hinges 22 preferably are provided between 12c and 12a to facilitate anterior movement of the posterior optic 12a.

Furthermore, the power of the present lens can be changed after implantation in the eye by either injecting or removing the liquid preferably silicone from the optic 10 or changing its refractive index.

The diameter of the portion 12d as well as its area can be less or more than that of the posterior portion 12a, dependent on the refractive range desired in the design of the lens.

As noted above, the haptics 16 may have a space or thin area 18 forming a hinge across their surface adjacent to the optic. This facilitates movement of the optic anteriorly and posteriorly relative to the outer ends of the haptics.

Figure 5:
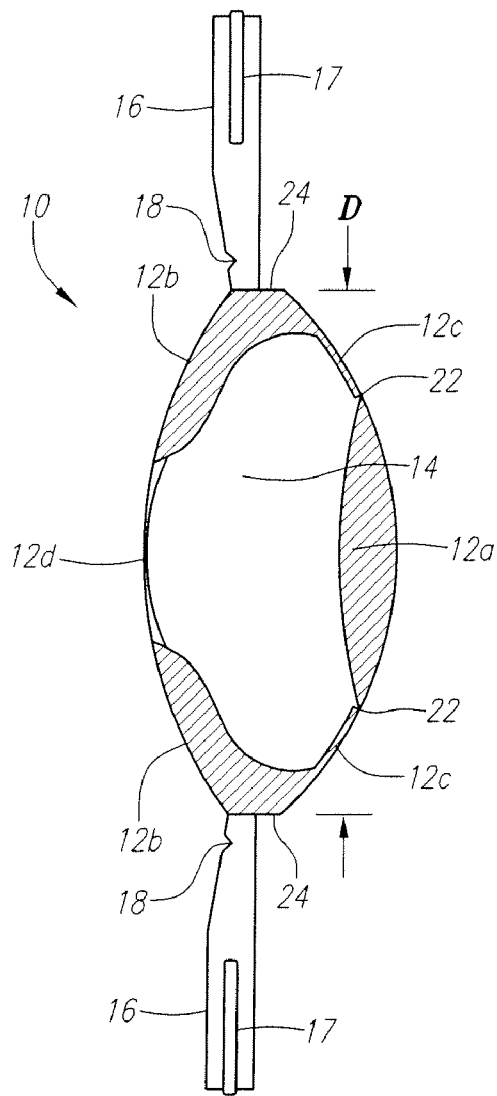
FIGS. 5 and 6 are variations in cross section.
Figure 6:
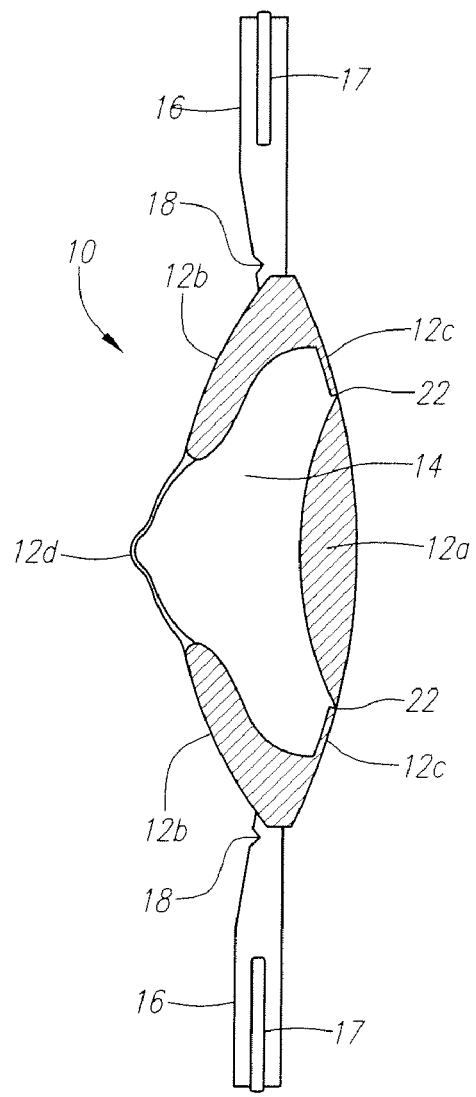

Turning now to the FIGS. 5-6 embodiment, it will be noted that anterior portion 12d is thinner in the middle, which will bulge more as shown in FIG. 6 under increased vitreous pressure. Alternatively, the portion 12d can have parallel sides, that is, not be thinner in the middle. Also, the back surface of portion 12a can be polyspheric or toric.

Turning now to FIGS. 7-8, these illustrate two further configurations. In FIGS. 7A and 7B the posterior center portion 12a is thin and not a large solid central portion like that shown in FIGS. 5 and 6. Also, anterior portion 12d is very thin, thinner than 12a, so as to enable bulging under increased vitreous pressure which at the same time causes indentation of the posterior thicker membrane 12a to change the refracting convex surface into a concave surface further increasing the power of the optic.

Figure 8A:
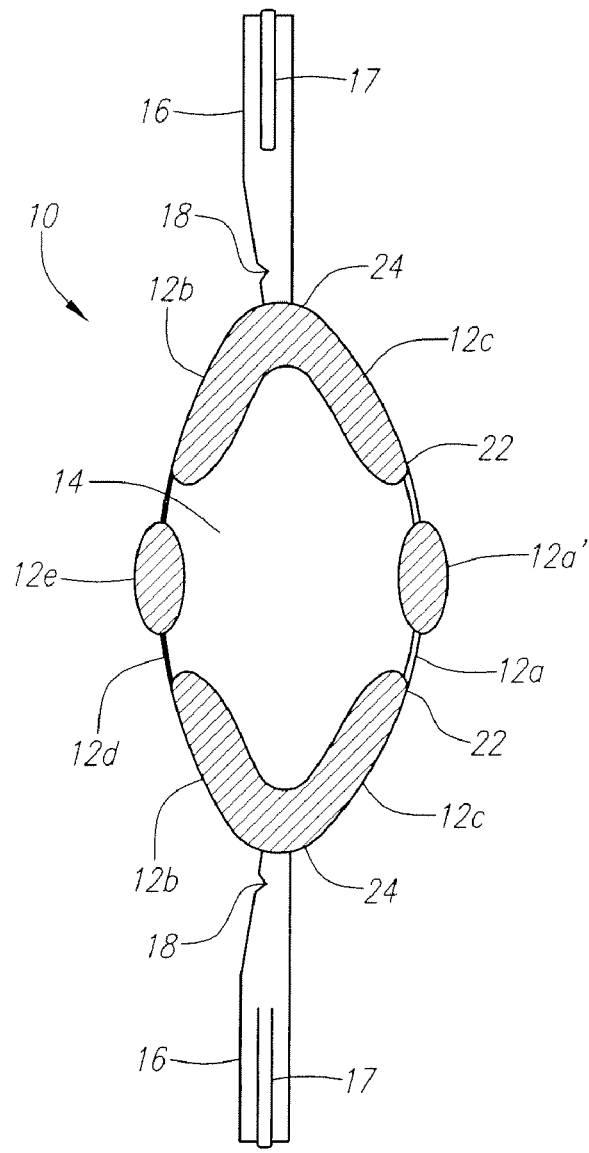

FIG. 8A is another alternative embodiment wherein both the posterior portion 12a' and anterior portion 12e comprise solid portions 12b and 12e, and the flexible annular portion 12a is thin and very flexible, and annular portion 12d is even thinner. An increase in vitreous pressure causes the portion 12e to move forward.

Figure 8B:
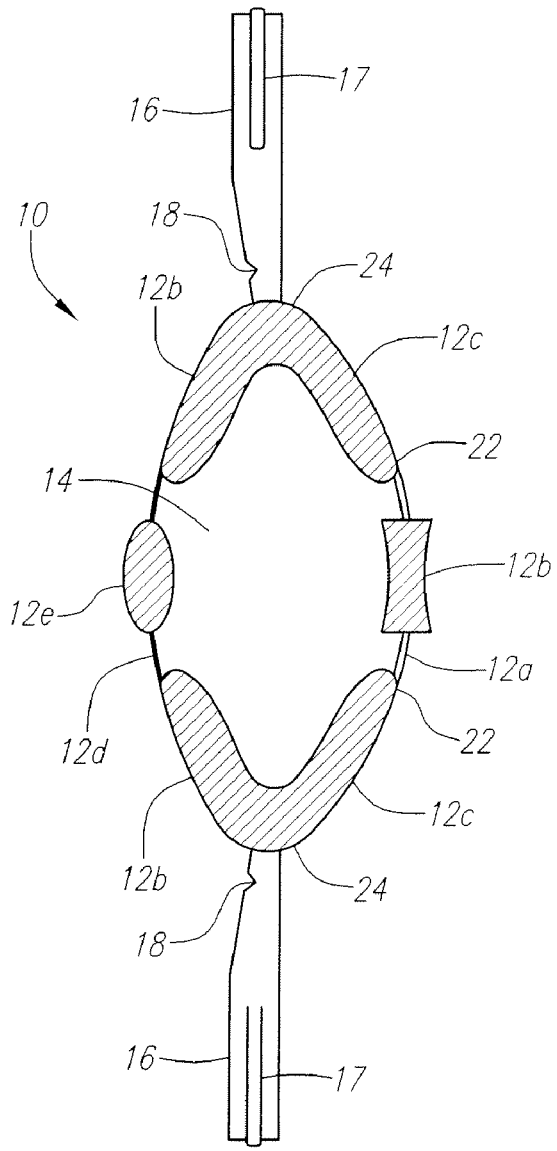
Figure 8C:
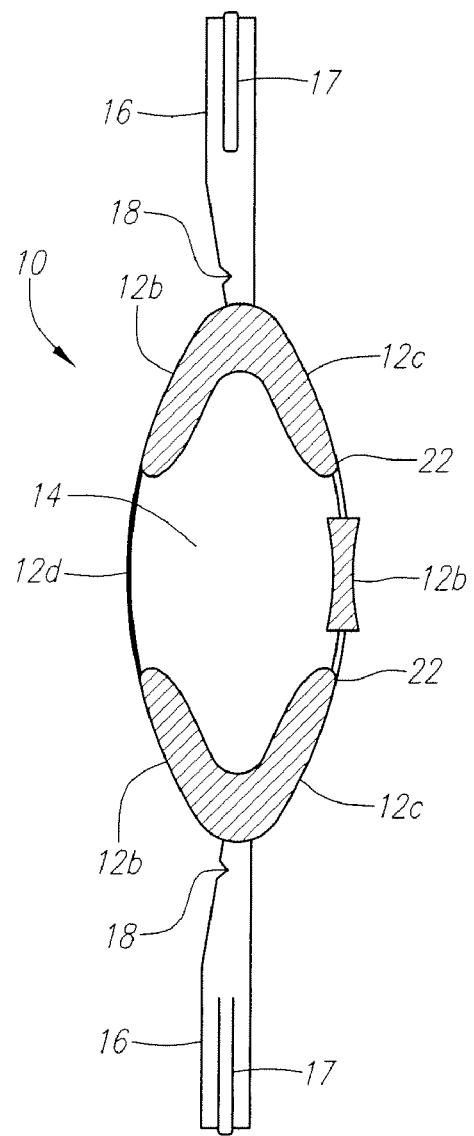
Figure 8D:
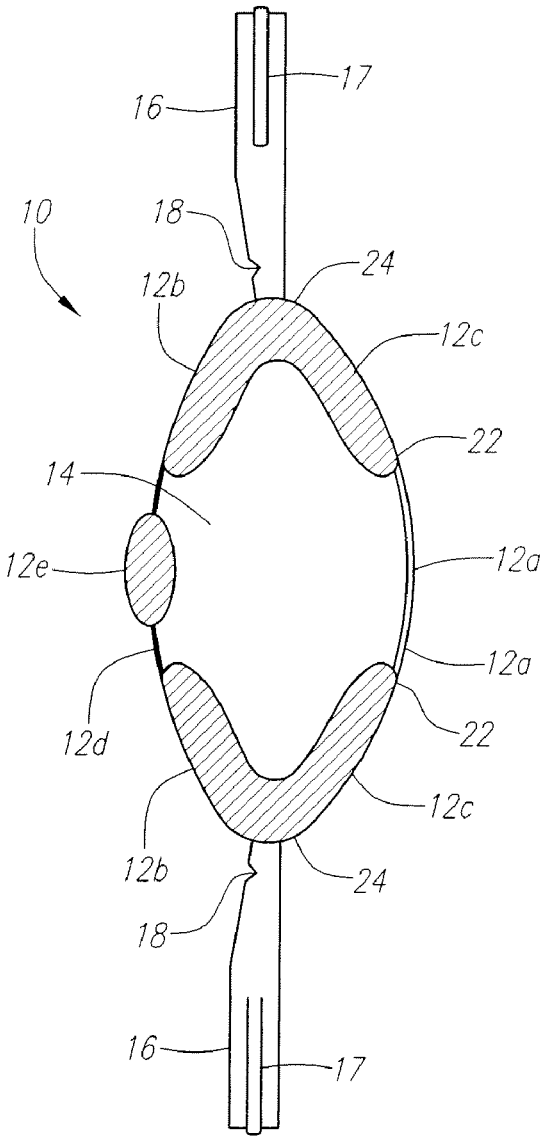

FIG. 8A demonstrates an optic with a convex solid optical surface on both the anterior 12e and posterior 12a' optical surfaces. FIG. 8B has a convex solid anterior optical surface 12e and a concave solid posterior optical surface 12b whereby more anterior movement of the anterior convex surface compared to a smaller movement of the posterior concave surface further increases the optical power of the lens. FIG. 8C is a further modification of the optic whereby the anterior optical surface 12d is thin and convex and the posterior solid optical surface 12b is concave. FIG. 8D is another variation with a thick posterior surface 12c and a thin convex solid anterior surface 12d.

Figure 9:
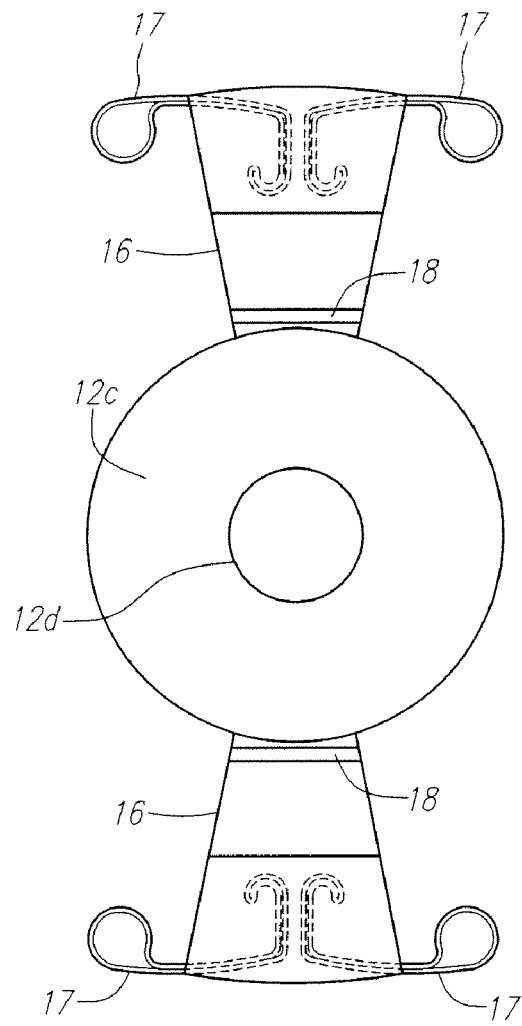
FIGS. 9-12 illustrate different forms of haptics that can be used on lenses of the present invention.
Figure 10:
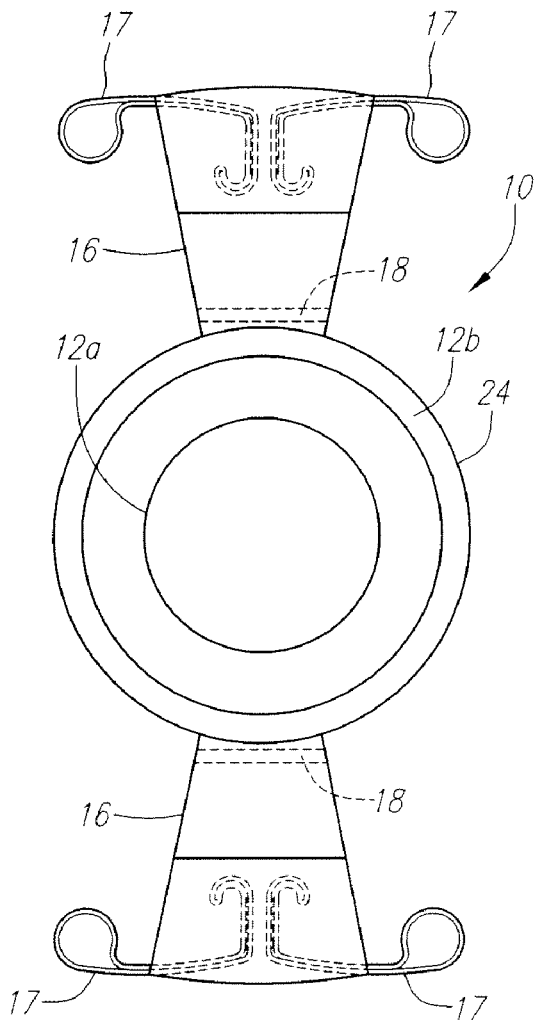
Figure 11:
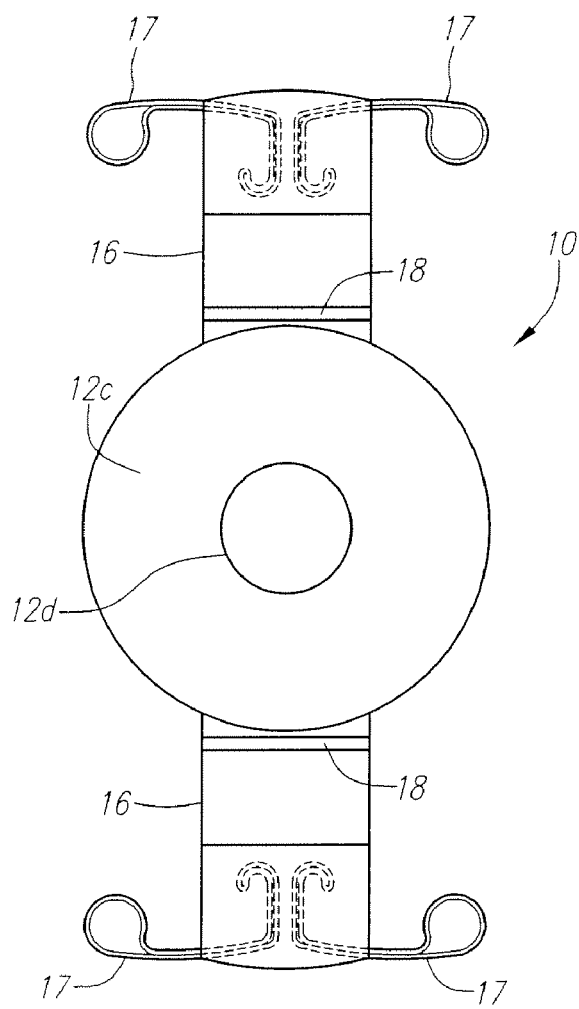
Figure 12:
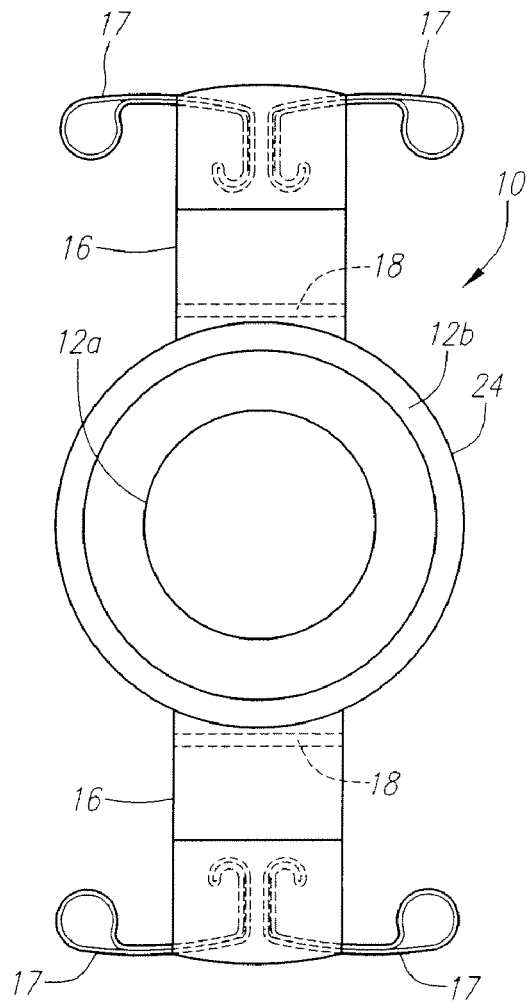

FIGS. 9-12 illustrate various different haptic arrangements for the lens embodiments herein. FIGS. 9 and 11 illustrate the anterior side of the lens and FIGS. 10 and 12 illustrate the posterior side. In each instance haptics 16 are provided which may be hinged at 18 to the optic. Preferably, flexible loops 17 are included at the ends of the haptics and are positioned in close proximity to, or to seat lightly against, the capsular bag cul-de-sac wall. The cul-de-sac wall deflects these loops inwardly slightly to better conform closely to the curvature of the cul-de-sac wall and accurately center the lens in the capsule bag.

As is well known in the art, an intraocular lens is implanted in the capsular bag of the eye after removal of the natural lens. The lens is inserted into the capsular bag by a generally circular opening cut in the anterior capsular bag of the human lens and through a small opening in the cornea or sclera. The outer ends of the haptics, or loops, are positioned in the cul-de-sac of the capsular bag. The outer ends of the haptics, or the loops, are in close proximity with the bag cul-de-sac, and in the case of any form of loops, the loops are deflected. Knobs can be provided on the outer end portions of the loops for improved securement in the capsular bag cul-de-sac with fibrosis, which develops in the capsular bag following the surgical removal of the central portion of the anterior capsular bag and the lens nucleus and cortex.

Accordingly, there has been shown and described a lens that comprises an optic of solid and liquid silicone and plate haptics or loops haptics, with preferably fixation and/or centration protuberances at the ends of each haptic plate.

Various changes, modifications, variations, and other uses and applications of the subject invention will become apparent to those skilled in the art after considering this specification together with the accompanying drawings and claims. All such changes, modifications, variations, and other uses of the applications which do not depart from the spirit and scope of the invention are intended to be covered by the claims which follow.

What is claimed is:

1. An accommodating intraocular lens in which the optic comprises an integral central optical system supported by a solid fixed radius, flexible annular peripheral optical component forming a solid annular support, a central anterior optical component comprising a thin deformable membrane, a central liquid optical material, and a posterior central flexible optic component and annulus suspended from the solid annular support, the flexible posterior component is thicker and less resilient than the thinner anterior membrane, the annulus being thicker than the anterior component, the posterior optic component being designed to move forward and compress the central liquid optical material to thereby cause the thin anterior membrane to bulge forward increasing the refractive power of the lens upon an increase of vitreous cavity pressure with ciliary muscle contraction, the optical system being designed such that anterior movement of the posterior optical component will result in an anterior component movement and increasing its curvature and decreasing the radius of the anterior component to increase the power of the optic.

2. The lens according to claim 1 wherein the posterior optic component is solid and convex.

3. The lens according to claim 1 wherein the posterior refracting surface is solid and concave.

4. The lens according to claim 1 wherein the posterior refracting surface is configured such that an increase in vitreous cavity pressure pushes the flexible posterior optic component forward.

5. The lens according to claim 1 wherein both the anterior and posterior refractive surfaces are convex and solid.

6. The lens according to claim 1 wherein the anterior refractive surface is convex and solid and the posterior refractive surface is concave and solid.

7. A lens according to claim 1 wherein one surface of the optical system is a membrane and the other a solid optical surface.

8. A lens according to claim 1 wherein the anterior and posterior surfaces are membranes.

9. A lens as in claim 1 wherein the whole optical system is designed to be supported within the eye by haptics.

10. A lens as in claim 9 wherein fixation devices are on the distal ends of the haptics.

11. A lens as in claim 9 wherein the haptics are plate haptics.

12. A lens as in claim 9 wherein the haptics have hinges adjacent the optical component.

13. A lens in claim 9 wherein the optical system is movable relative to the outer ends of the haptics.

14. An accommodating intraocular lens having an optic formed of solid silicone and liquid silicone, the optic being circular and having a solid peripheral annular portion extending to anterior and posterior surfaces of the optic, the optic having a central anterior portion, and a central posterior portion, the central anterior portion comprising a very thin portion and the central posterior portion comprising a solid central optical portion surrounded by an annular membrane thicker than the anterior portion, the optic being designed so that the thin anterior portion can change in radius of curvature upon an increase in vitreous cavity pressure on the posterior solid optic portion, the optical system being designed such that anterior movement of the posterior optical component will result in an anterior component movement and increasing its curvature and decreasing the radius of the anterior component to increase the power of the optic.

15. The lens as in claim 14 further including extending portions from an edge of the optic for facilitating placement of the lens in an eye.

16. The lens as in claim 15 wherein the extending portions are haptics.

17. The lens as in claim 15 wherein the extending portions are plate haptics.

18. The lens as in claim 15 wherein the optic can move anteriorly and posteriorly relative to the outer ends of the extending portions.

19. The lens as in claim 14 wherein the solid silicone and the liquid silicone have approximately the same specific gravity as the aqueous solution of a human eye.

20. The lens as in claim 14 designed such that compression of the posterior surface of the posterior portion by vitreous pressure can cause bulging of an anterior surface of the central anterior portion.

21. The lens as in claim 14 wherein the solid and liquid portions of the optic have substantially the same index of refraction.

22. The lens as in claim 14 wherein the liquid has a different refractive index than the solid optical components of the optic.

23. The lens as in claim 14 wherein the optic has radii of curvature to give a patient within whom the lens is to be implanted emmetropia upon relaxation of the ciliary muscle.

24. The lens as in claim 14 wherein the thin central anterior portion has a smaller area than the central posterior portion.

25. The lens as in claim 14 wherein the thin central anterior portion has a larger area than the central posterior portion.

26. A combination accommodating intraocular lens having an optic which comprises an integral central optical system supported by a solid fixed radius, flexible annular peripheral optical component forming a solid annular support, the optic formed of both solid and liquid silicone with thin single silicone membranes on both a posterior portion and an anterior portion of the lens, the liquid silicone being contained between the posterior and anterior portions, the membrane on the anterior portion is centered and the posterior membrane is annular and peripheral to a solid convex optical surface, the anterior membrane is thinner than the posterior membrane and capable of bulging to change power upon compression of the posterior portion by vitreous pressure, the optical system being designed such that anterior movement of the posterior optical component will result in an anterior component movement and increasing its curvature and decreasing the radius of the anterior component to increase the power of the optic.

27. A lens as in claim 26 wherein the lens includes extending portions from the optic for facilitating placement of the lens in an eye.

28. A lens as in claim 27 wherein the extending portions are plate haptics.

29. A lens as in claim 28 wherein the haptics have a hinge adjacent to the optic.

30. A lens as in claim 26 wherein the posterior membrane extends between a posterior axial portion and posterior and anterior solid outer portions of the optic, and the thin membrane of the anterior portion is centered on an anterior side of the lens.

31. An accommodating intraocular lens having an optic which comprises an integral central optical system supported by a solid fixed radius, flexible annular peripheral optical component, a central anterior optical component comprising a thin deformable membrane, and a posterior central solid flexible optical component and annulus suspended from the peripheral optical component which is thicker and less resilient than the thinner anterior membrane, a central liquid optical material contained between the anterior and posterior components, the posterior component being designed to move forward and compress the central liquid optical material to thereby cause the thin anterior membrane to bulge forward thereby decreasing its radius of curvature and increasing its refractive power upon an increase of vitreous cavity pressure with ciliary muscle contraction, and the optical system being designed such that anterior movement of the posterior optical component will result in an anterior component movement and increasing its curvature and decreasing the radius of the anterior component to increase the power of the optic.

32. A lens as in claim 31 wherein the whole optical system is designed to be supported within the eye by haptics.

33. A lens as in claim 32 wherein fixation devices are on the distal ends of the haptics.

34. A lens as in claim 32 wherein the haptics are plate haptics.

35. A lens as in claim 32 wherein the haptics have hinges adjacent the optic.

* * * * *